US011938749B2

(12) United States Patent
Genovese

(10) Patent No.: US 11,938,749 B2
(45) Date of Patent: Mar. 26, 2024

(54) DEVICES AND METHODS FOR ASSISTING A USER TO MANIPULATE AN INSTRUMENT

(71) Applicant: Lianna Genovese, Hamilton (CA)

(72) Inventor: Lianna Genovese, Hamilton (CA)

(73) Assignee: 11486934 Canada Inc., Hamilton (CA)

( * ) Notice: Subject to any disclaimer, the term of this patent is extended or adjusted under 35 U.S.C. 154(b) by 660 days.

(21) Appl. No.: 17/162,316

(22) Filed: Jan. 29, 2021

(65) Prior Publication Data

US 2021/0229486 A1 Jul. 29, 2021

Related U.S. Application Data

(60) Provisional application No. 62/967,228, filed on Jan. 29, 2020.

(51) Int. Cl.
*B43K 23/004* (2006.01)
*A61F 4/00* (2006.01)
*B43K 23/00* (2006.01)

(52) U.S. Cl.
CPC .............. *B43K 23/004* (2013.01); *A61F 4/00* (2013.01); *B43K 23/002* (2013.01)

(58) Field of Classification Search
CPC ............................ B43K 23/002; B43K 23/004
USPC ........................................................... 33/18.1
See application file for complete search history.

(56) References Cited

U.S. PATENT DOCUMENTS

| 1,607,376 | A | * | 11/1926 | Willson | B43L 13/10 |
| | | | | | 33/23.06 |
| 2,785,462 | A | * | 3/1957 | Barg | B43L 15/00 |
| | | | | | 30/296.1 |
| 4,087,916 | A | | 5/1978 | Goguillot | |
| 4,095,906 | A | | 6/1978 | Sackett | |
| 4,165,896 | A | | 8/1979 | Hunt | |
| 4,447,912 | A | * | 5/1984 | Morrow | A61F 4/00 |
| | | | | | 2/160 |
| 4,558,522 | A | | 12/1985 | Lance | |
| 4,683,836 | A | | 8/1987 | West | |
| 4,713,887 | A | * | 12/1987 | Kitamura | B44B 3/02 |
| | | | | | 33/18.1 |
| 4,944,766 | A | * | 7/1990 | Williams | A61F 4/00 |
| | | | | | 401/6 |
| 5,141,198 | A | * | 8/1992 | Hoyt | B43L 15/00 |
| | | | | | 248/460 |
| 5,180,239 | A | | 1/1993 | Bistrack | |
| 5,193,772 | A | * | 3/1993 | Johnston | B43L 5/002 |
| | | | | | 248/441.1 |
| 5,791,705 | A | | 8/1998 | Romero et al. | |

(Continued)

FOREIGN PATENT DOCUMENTS

DE 102009042731 A1 4/2011

*Primary Examiner* — George B Bennett

(74) *Attorney, Agent, or Firm* — Bereskin & Parr LLP

(57) ABSTRACT

A device for assisting a user to manipulate an instrument to interact with an object resting on a surface is described herein. The device includes a framework for resting on the surface and a hand and wrist support. The hand and wrist support is coupled to the framework, coupled to the instrument and vertically spaced above the surface. The hand and wrist support is configured to slide horizontally and longitudinally along the framework and rotate about the framework to provide for the user to move the hand and wrist support to manipulate the instrument to interact with the object.

15 Claims, 20 Drawing Sheets

(56) References Cited

U.S. PATENT DOCUMENTS

| | | | |
|---|---|---|---|
| 6,691,972 B1 * | 2/2004 | Oliver | A47B 97/04 248/118.5 |
| 7,694,931 B2 | 4/2010 | Mantelli | |
| 8,393,812 B2 | 3/2013 | Shultz | |
| 9,221,296 B2 * | 12/2015 | Duffy | A47B 97/04 |
| 11,789,483 B2 * | 10/2023 | Ruegsegger | A61F 4/00 74/494 |
| 2006/0130347 A1 * | 6/2006 | Bergamasco | A61B 5/1071 33/512 |
| 2006/0174449 A1 * | 8/2006 | Hughes | A61F 4/00 16/110.1 |
| 2007/0020021 A1 * | 1/2007 | Snyder | B43M 7/007 401/48 |
| 2013/0209155 A1 | 8/2013 | Dunne | |
| 2015/0094636 A1 | 4/2015 | Miyazawa | |
| 2015/0300394 A1 | 10/2015 | Pathak | |
| 2016/0019809 A1 * | 1/2016 | Schlosser | G09B 11/02 30/340 |
| 2017/0157774 A1 | 6/2017 | Pathak et al. | |
| 2018/0064597 A1 | 3/2018 | Pathak et al. | |
| 2018/0093125 A1 | 4/2018 | Johnson | |
| 2019/0000251 A1 | 1/2019 | Pathak | |
| 2019/0099473 A1 | 4/2019 | Fujita et al. | |
| 2019/0101983 A1 | 4/2019 | Cohen et al. | |
| 2019/0366086 A1 | 12/2019 | Creasey et al. | |
| 2021/0228390 A1 * | 7/2021 | Shepherd | A61F 4/00 |

\* cited by examiner

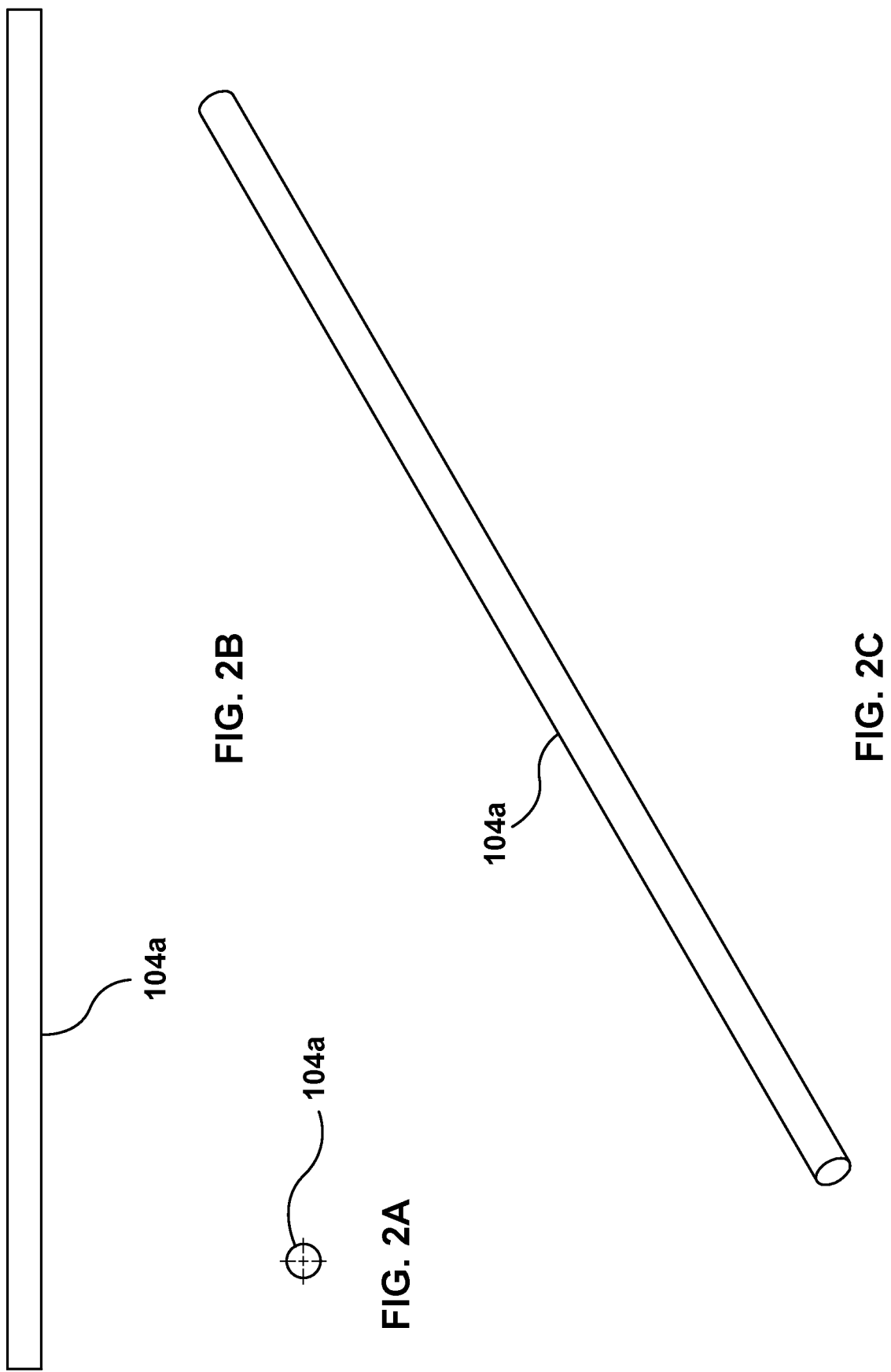

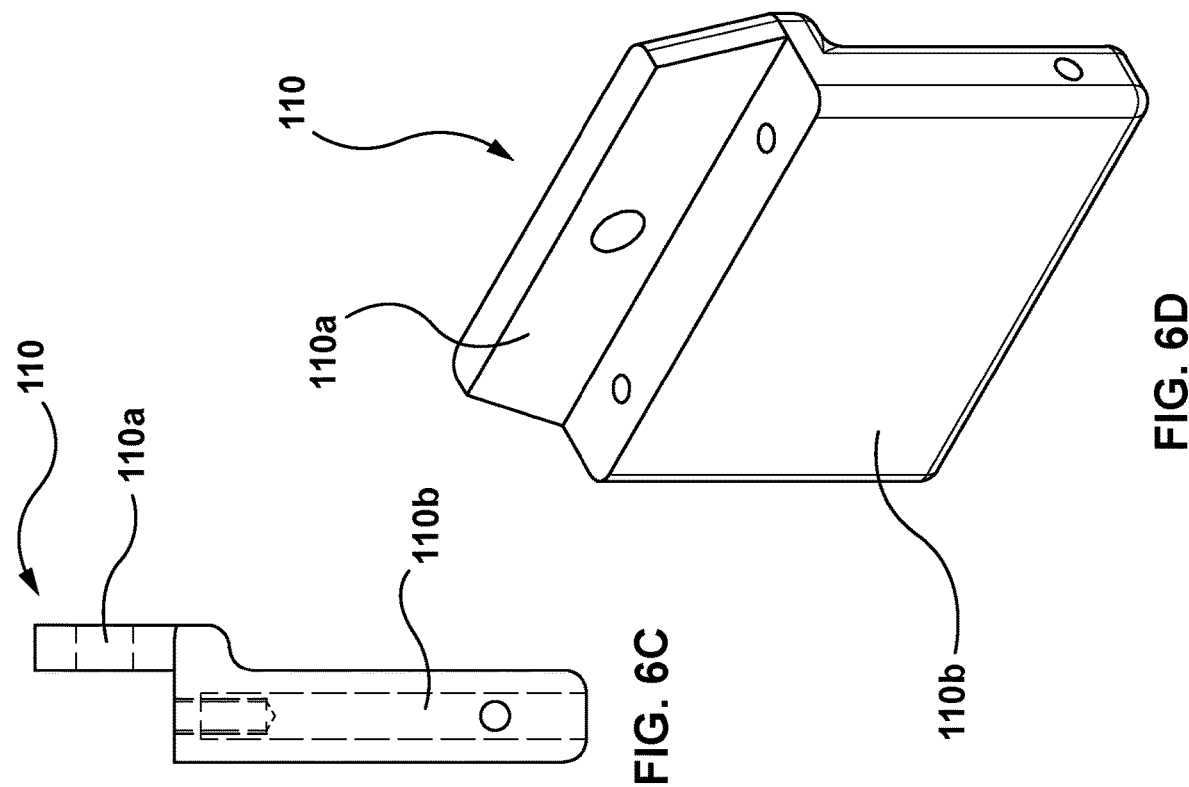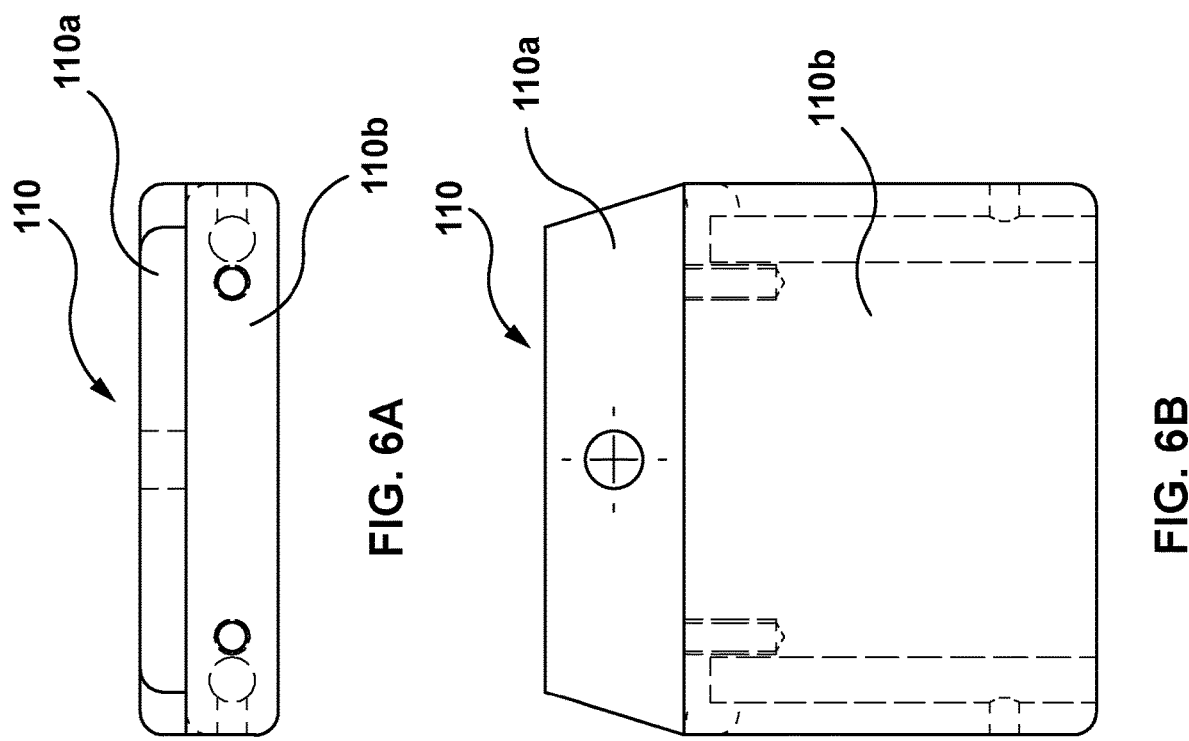

DEVICES AND METHODS FOR ASSISTING A USER TO MANIPULATE AN INSTRUMENT

CROSS-REFERENCE

This application claims the benefit of U.S. Provisional Patent Application No. 62/967,228, filed Jan. 29, 2020 and entitled "Devices and Methods for Assisting a User to Manipulate an Instrument", the contents of which are hereby incorporated by reference.

FIELD

The embodiments disclosed herein relate to devices and methods for assisting a user to manipulate an instrument, and more specifically to devices and methods for assisting users with limited hand skills to write, paint, draw, and/or use a tablet/computer.

BACKGROUND

A common problem for individuals with conditions that limit basic hand function, and particularly fine motor hand skills, is the inability to write, paint, draw, and/or use a tablet/computer. Although some may consider these to be mundane activities, for individuals with limited fine motor hand skills, these can be essential activities that represent the individual's independence.

Existing technologies that aim to assist users with limited fine motor hand skills to write, paint, draw, and/or use a tablet/computer typically include wearable devices that do not reduce hand fatigue and/or provide pain relief to users, do not provide guided hand movements to users and do not include customizable and interchangeable component pieces.

Accordingly, there is a need for new devices and methods for assisting users with limited fine motor hand skills to write, paint, draw, and/or use a tablet/computer.

SUMMARY

Devices for assisting a user to manipulate an instrument to interact with an object resting on a surface are described herein. The devices include a framework for resting on the surface and a hand and wrist support coupled to the framework, coupled to the instrument and vertically spaced above the surface. The hand and wrist support is configured to slide horizontally and longitudinally along the framework and rotate about the framework to provide for the user to move the hand and wrist support to manipulate the instrument to interact with the object.

In some embodiments, the framework comprises two lateral supports spaced apart from each other; and a crossing support coupled to each of the two lateral supports and coupled to the hand and wrist support, the crossing support being vertically spaced above the surface.

In some embodiments, the crossing support is configured to slide horizontally and longitudinally along the two lateral supports.

In some embodiments, the crossing support defines a first axis and the hand and wrist support is configured to slide along the crossing support.

In some embodiments, the hand and wrist support is configured to rotate about the crossing support.

In some embodiments, the device includes a swivel coupled to the hand and wrist support and the crossing support to provide for the hand and wrist support to rotate about the crossing support.

In some embodiments, the framework further comprises a base for resting on the surface and supporting the object.

In some embodiments, the hand and wrist support includes a wrist plate coupled to the crossing support for supporting a wrist of the user above the surface and a hand support coupled to the wrist plate for supporting a hand of the user above the surface.

In some embodiments, the hand and wrist support further includes an instrument retainer for movably coupling the instrument to the hand support.

In some embodiments, the instrument retainer includes a flexible linkage coupled to the hand support and a clamp coupled to the flexible linkage, the clamp configured to retain the instrument.

In some embodiments, the hand support is shaped to provide for a user to curl their fingers around a top end of the hand support to grip the hand support.

In some embodiments, the hand support has a semi-spherical shape.

In some embodiments, the hand support is releasably coupled to the plate by a connector.

In some embodiments, the connector and the hand support are configured to releasably couple to each other by friction.

In some embodiments, the connector includes a recess and the hand support includes a protruding portion, the protruding portion being sized and shaped to fit within the recess to releasably couple the hand support to the connecting piece by friction.

These and other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 2A is an end view of a lateral support of the device of FIG. 1A, according to at least one embodiment.

FIG. 2B is a side view of the lateral support of FIG. 2A.

FIG. 2C is a perspective view of the lateral support of FIG. 2A.

FIG. 6A is a top view of a wrist plate of a hand and wrist support of the device of FIG. 1A, according to at least one embodiment.

FIG. 6B is a front view of the wrist plate of FIG. 6A.

FIG. 6C is an end view of the wrist plate of FIG. 6A.

FIG. 6D is a perspective view of the wrist plate of FIG. 6A.

Figure 1A:
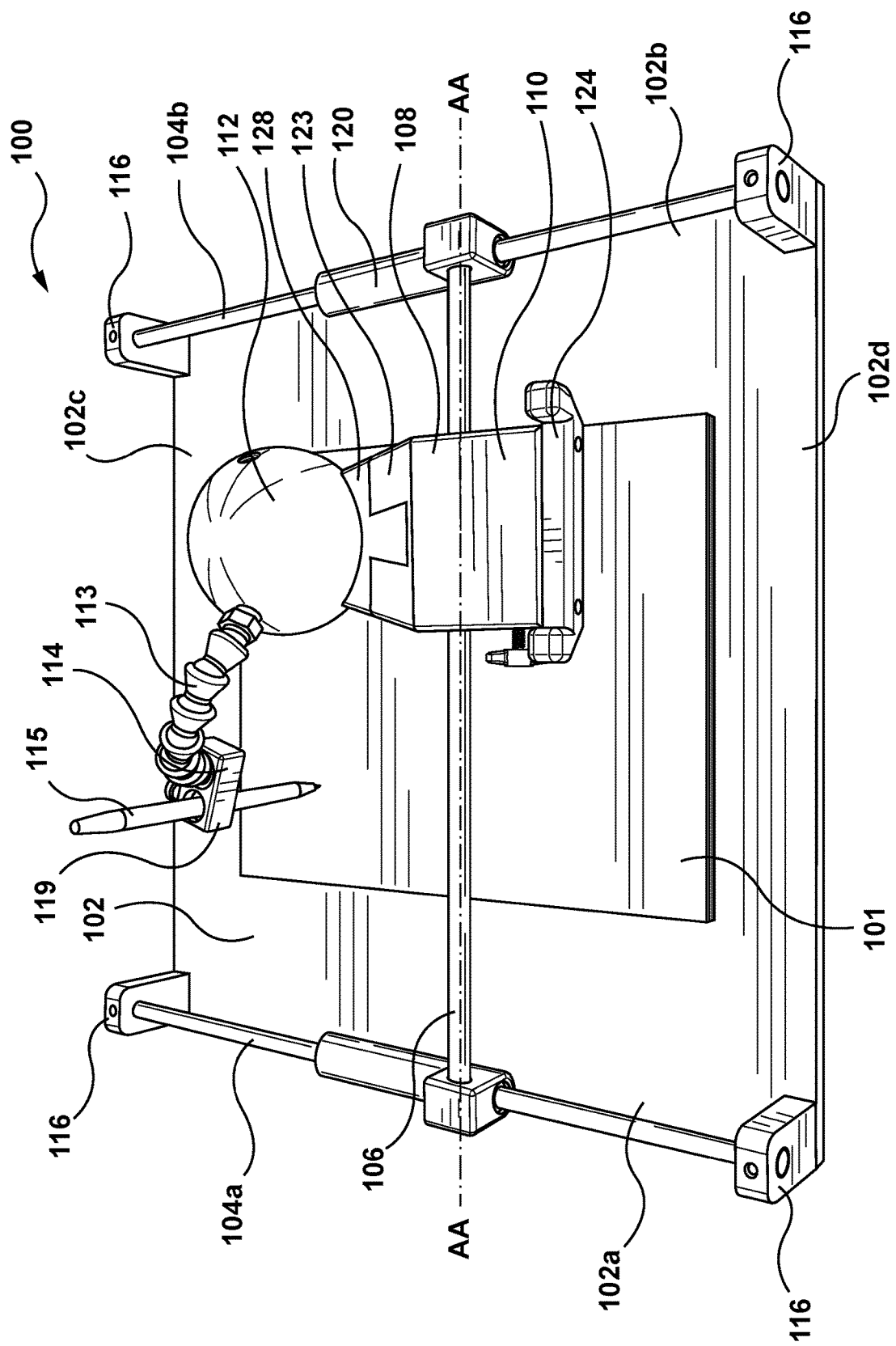
FIG. 1A is perspective view of a device for assisting a user to manipulate an instrument to interact with an object resting on a surface, according to at least one embodiment.

Further aspects and features of the example embodiments described herein will appear from the following description taken together with the accompanying drawings.

DETAILED DESCRIPTION

Various apparatuses, methods and compositions are described below to provide an example of at least one embodiment of the claimed subject matter. No embodiment described below limits any claimed subject matter and any claimed subject matter may cover apparatuses and methods that differ from those described below. The claimed subject matter are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed subject matter. Any subject matter that is disclosed in an apparatus, method or composition described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the end result is not significantly changed. These terms of degree should be construed as including a deviation of the modified term, such as 1%, 2%, 5%, or 10%, for example, if this deviation does not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as 1%, 2%, 5%, or 10%, for example, if the end result is not significantly changed.

It should also be noted that, as used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

The following description is not intended to limit or define any claimed or as yet unclaimed subject matter. Subject matter that may be claimed may reside in any combination or sub-combination of the elements or process steps disclosed in any part of this document including its claims and figures. Accordingly, it will be appreciated by a person skilled in the art that an apparatus, system or method disclosed in accordance with the teachings herein may embody any one or more of the features contained herein and that the features may be used in any particular combination or sub-combination that is physically feasible and realizable for its intended purpose.

Recently, there has been a growing interest in developing new technologies for assisting users, such as users with limited hand skills, to manipulate an instrument.

Accordingly, devices and methods for assisting a user to manipulate an instrument are described herein.

In some embodiments, the assistive devices described herein assist users with limited fine motor skills to write, paint, draw, and/or use a tablet/computer or the like. The assistive devices described herein may reduce pain and/or hand fatigue of the user and/or promote guided hand movements of the user while writing, painting, drawing, and/or using a tablet/computer or the like.

In some embodiments, the assistive devices described herein are mechanical devices that use a system of bearings, shafts, and/or one or more custom 3D-printed hand pieces to assist users to write, paint, draw, and/or use a tablet/computer or the like. Although bearings are described herein for providing ease of motion between two structures (e.g. to reduce friction), it should be noted that any bearings may be replaced by other structures or compositions for reducing friction between two components.

In some embodiments, the assistive devices described herein may improve hand coordination of users with limited fine motor skills and may provide for users with limited fine motor skills to easily and ergonomically hold a utensil or an instrument of choice while writing, painting, drawing, and/ or using a tablet/computer or the like.

Figure 1B:
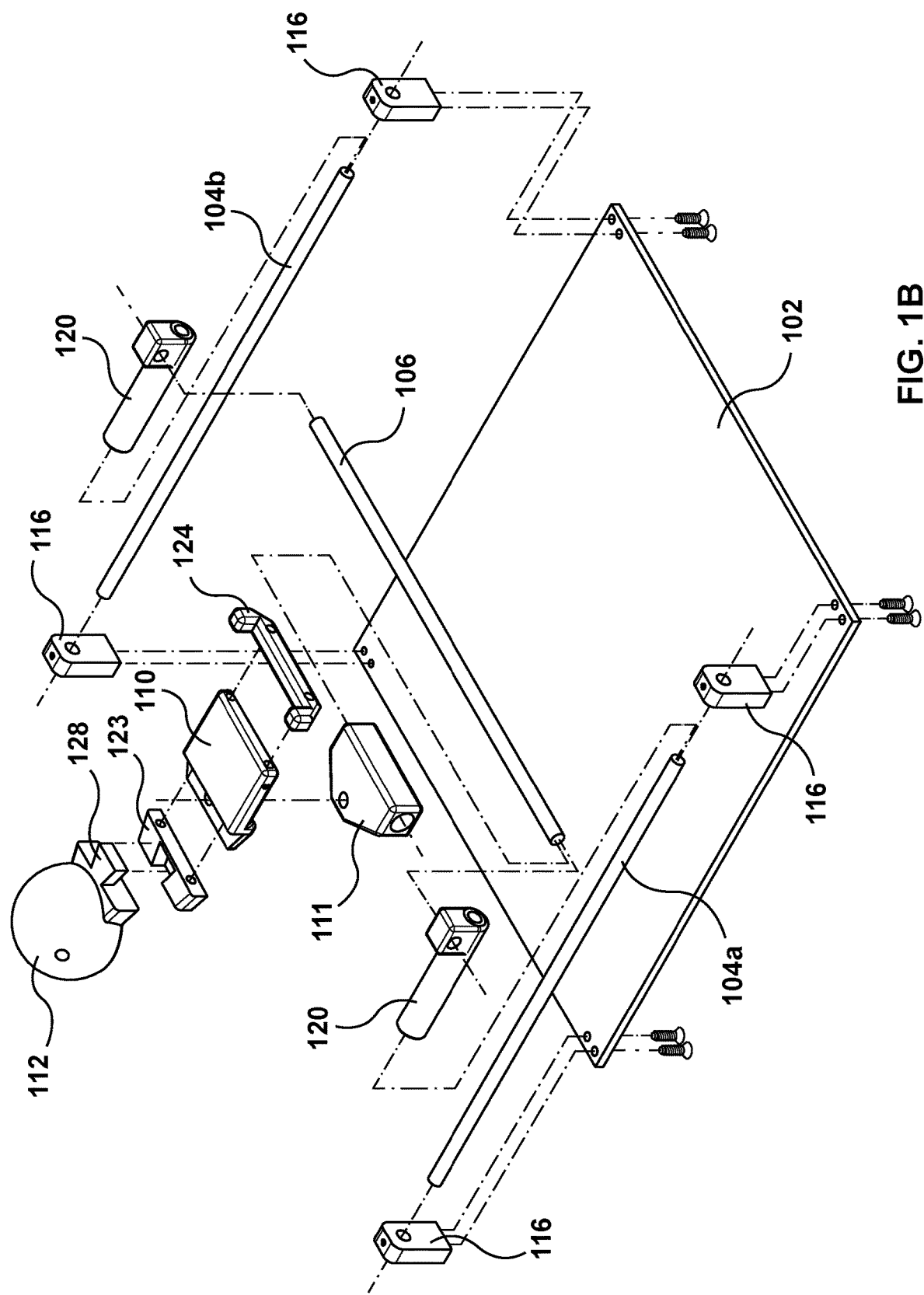
FIG. 1B is an exploded perspective view of the device for assisting a user to manipulate an instrument to interact with an object of FIG. 1A.
Figure 3D:
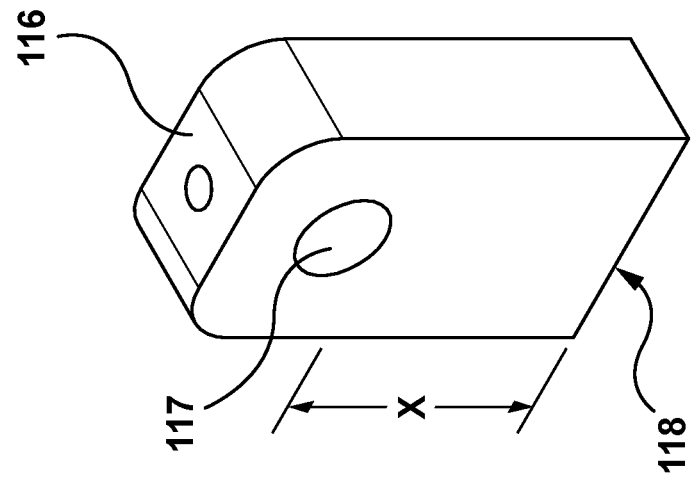
FIG. 3D is a perspective view of the stand of FIG. 3A.
Figure 3C:
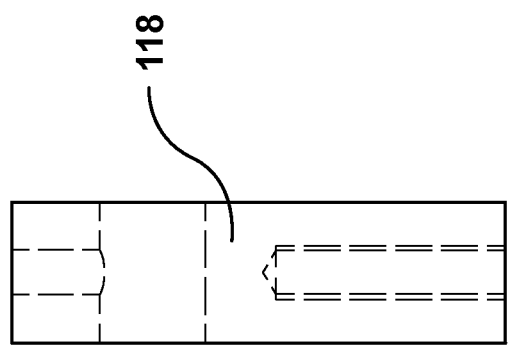
FIG. 3C is a front view of the stand of FIG. 3A.
Figure 3A:
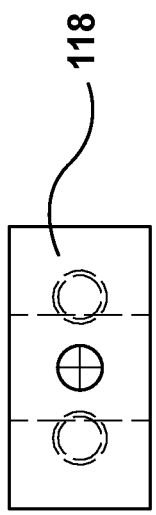
FIG. 3A is top view of a stand of the device of FIG. 1, according to at least one embodiment.
Figure 3B:
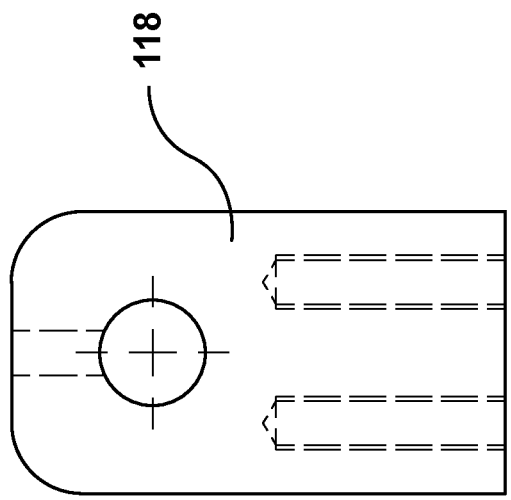
FIG. 3B is an end view of the stand of FIG. 3A.
Figure 4A:
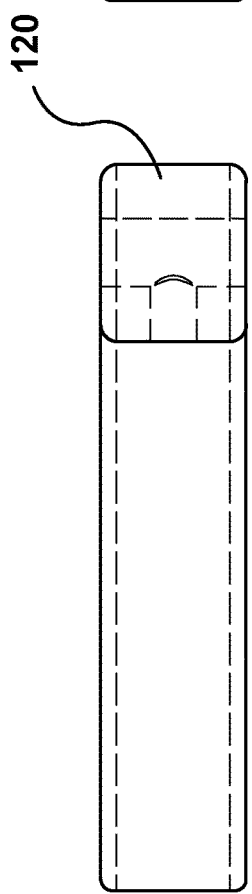
FIG. 4A is top view of a housing of the device of FIG. 1A, according to at least one embodiment.
Figure 4B:
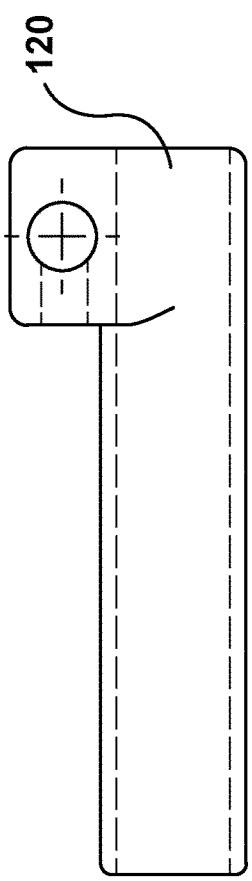
FIG. 4B is a side view of the housing of FIG. 4A.
Figure 4C:
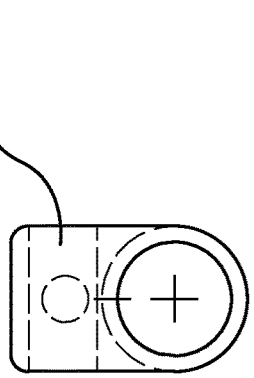
FIG. 4C is an end view of the housing of FIG. 4B.
Figure 4D:
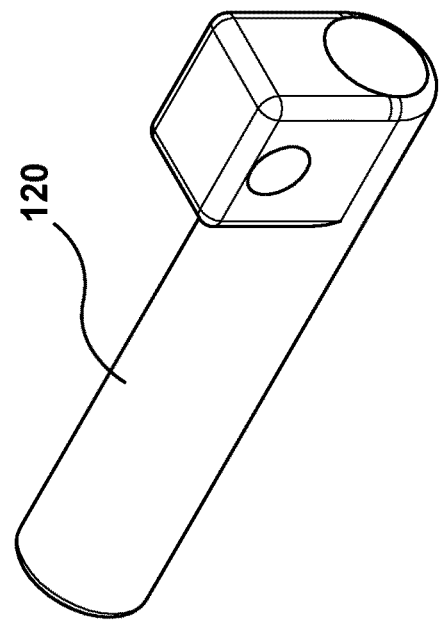
FIG. 4D is a perspective view of the housing of FIG. 4B.
Figure 5B:
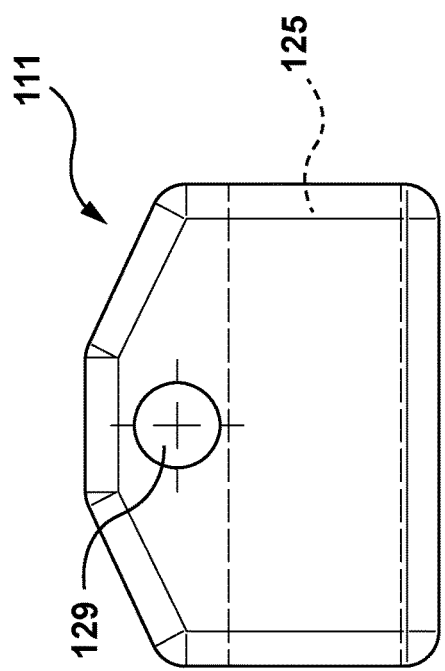
FIG. 5B is a front view of the swivel of FIG. 5A.
Figure 5D:
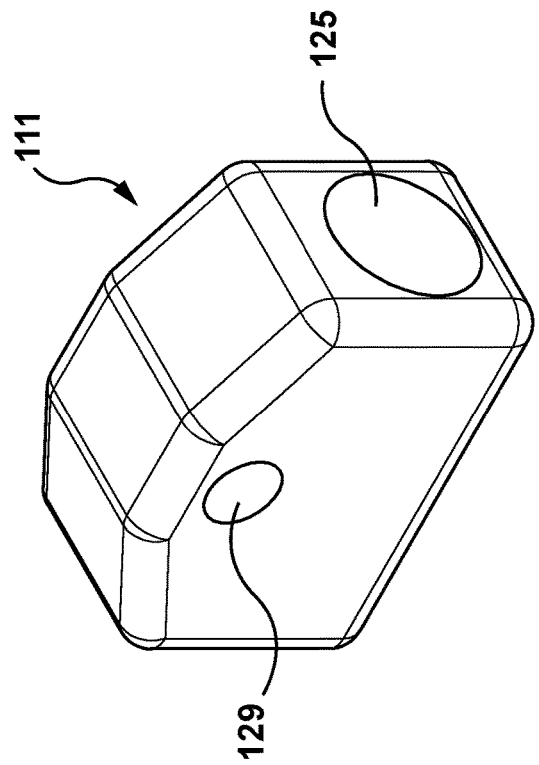
FIG. 5D is a perspective view of the swivel of FIG. 5A.
Figure 5A:
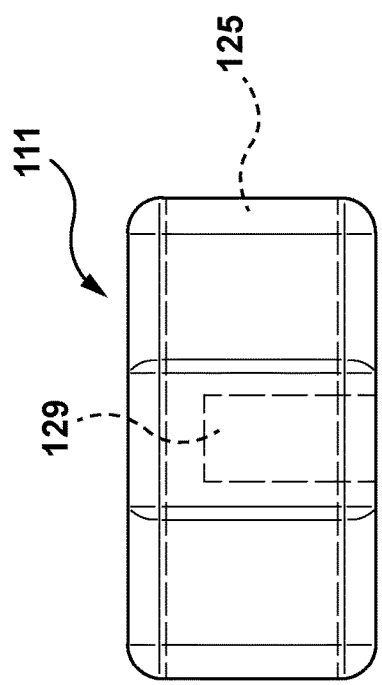
FIG. 5A is a top view of a swivel of the device of FIG. 1A, according to at least one embodiment.
Figure 5C:
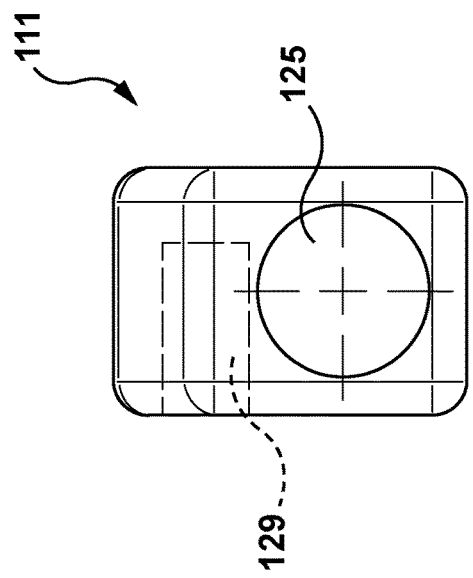
FIG. 5C is an end view of the swivel of FIG. 5A.
Figure 7B:
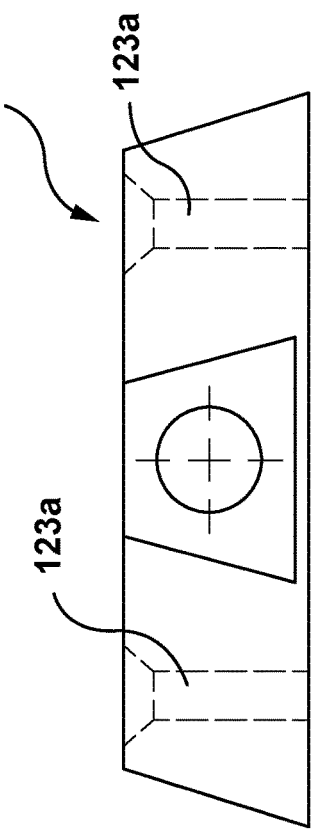
FIG. 7B is a front view of the connector of FIG. 7A.
Figure 7D:
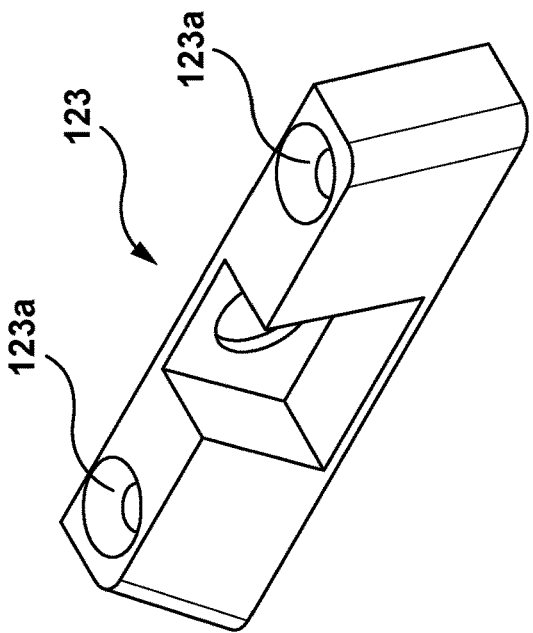
FIG. 7D is a perspective view of the connector of FIG. 7A.
Figure 7A:
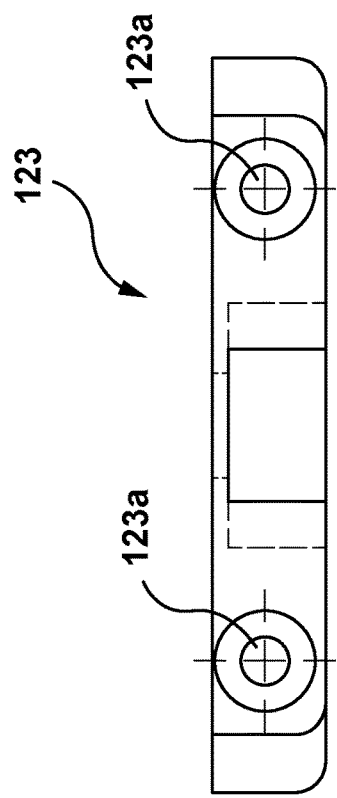
FIG. 7A is a top view of a connector of a hand and wrist support of the device of FIG. 1A, according to at least one embodiment.
Figure 7C:
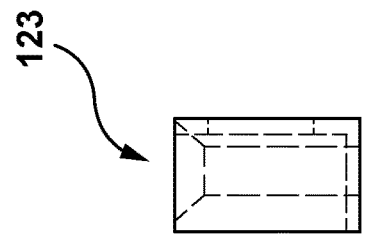
FIG. 7C is an end view of the connector of FIG. 7A.
Figure 8B:
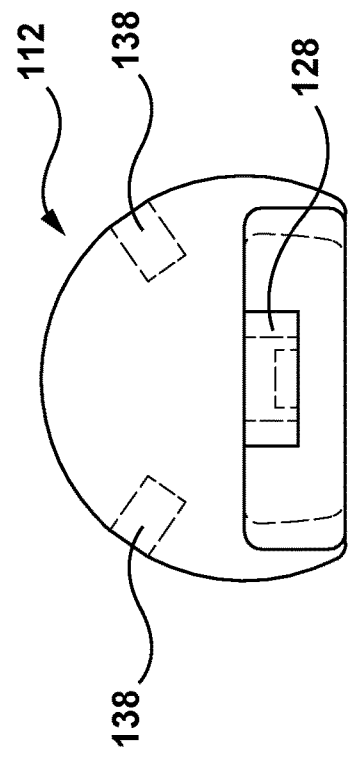
FIG. 8B is a front view of the hand support of FIG. 1A.
Figure 8D:
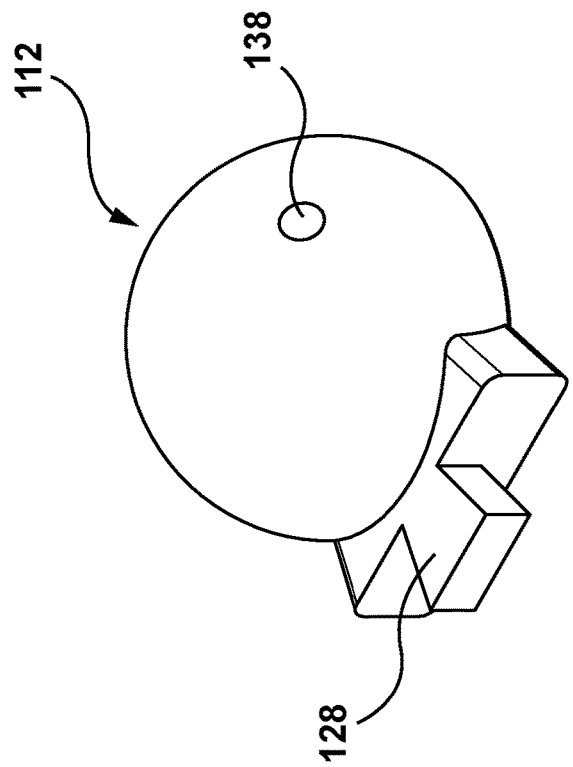
FIG. 8D is a perspective view of the hand support of FIG. 1A.
Figure 8A:
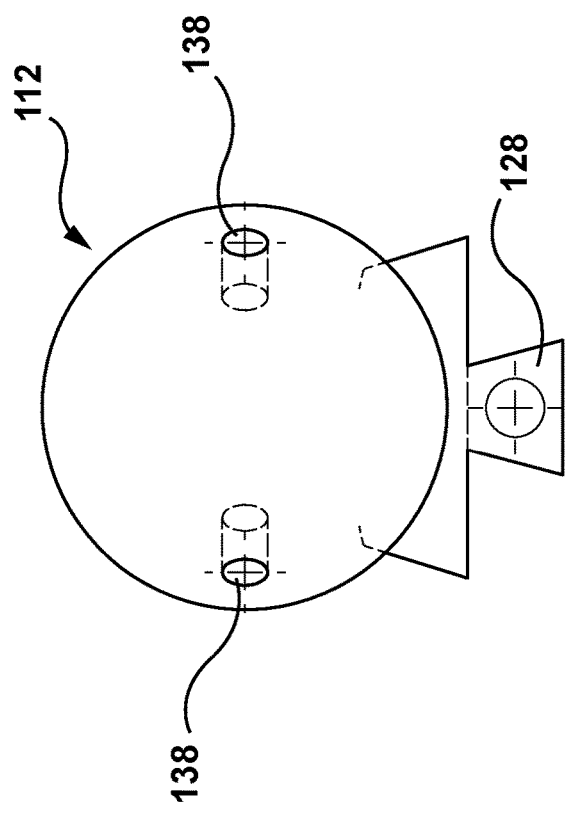
FIG. 8A is a top view of a hand support of the device of FIG. 1A, according to one embodiment.
Figure 8C:
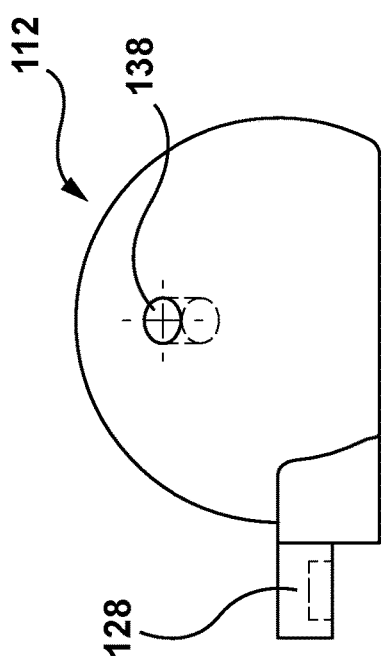
FIG. 8C is a side view of the hand support of FIG. 1A.
Figure 9A:
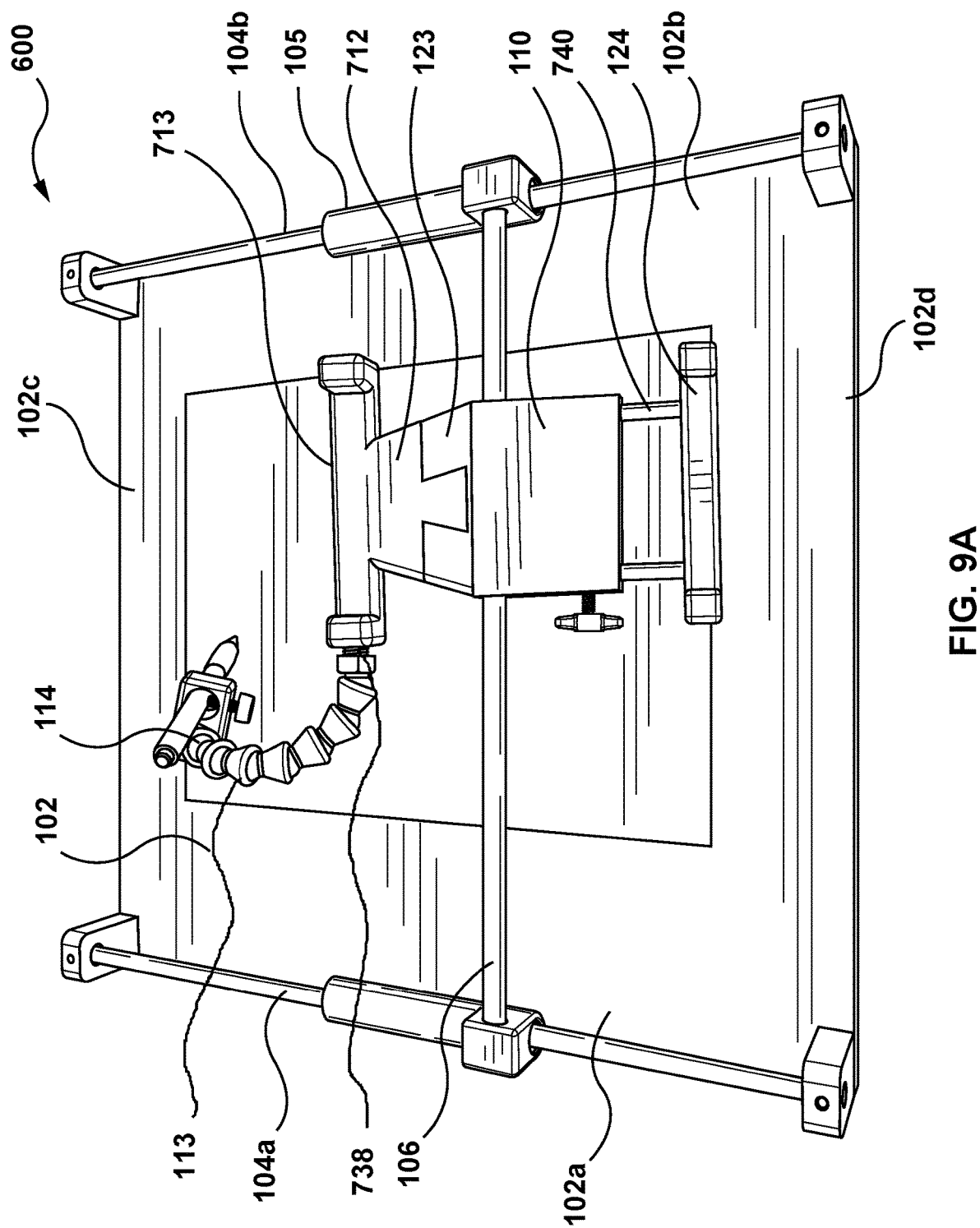
FIG. 9A is a perspective view of a device for assisting a user to manipulate an instrument to interact with an object resting on a surface, according to at least one embodiment.
Figure 9B:
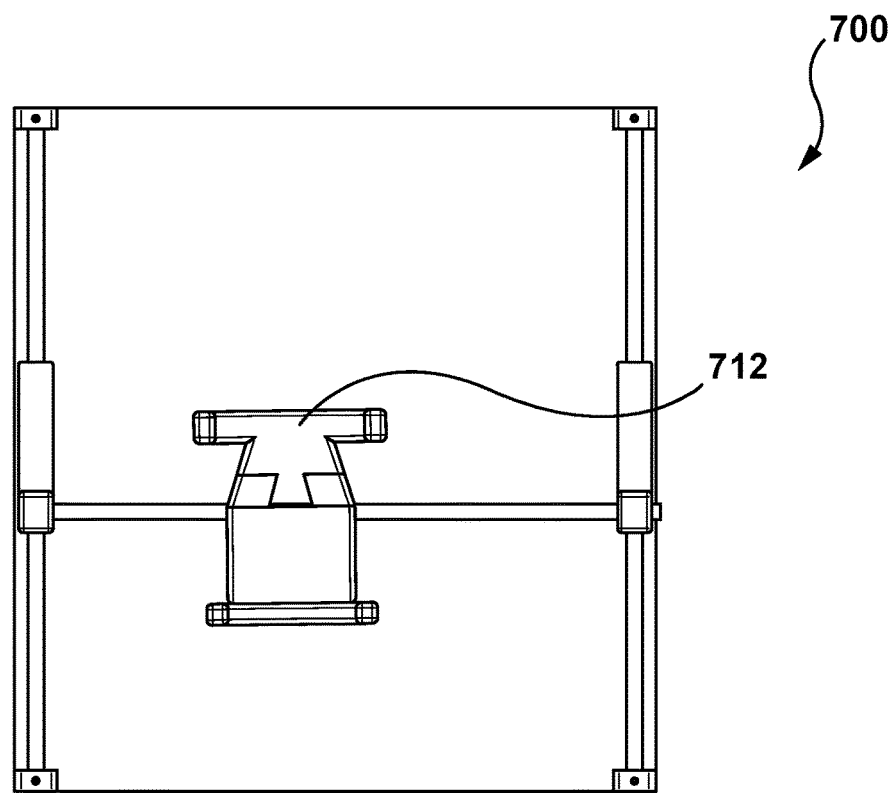
FIG. 9B is a schematic top view of the device of FIG. 9A.
Figure 9C:
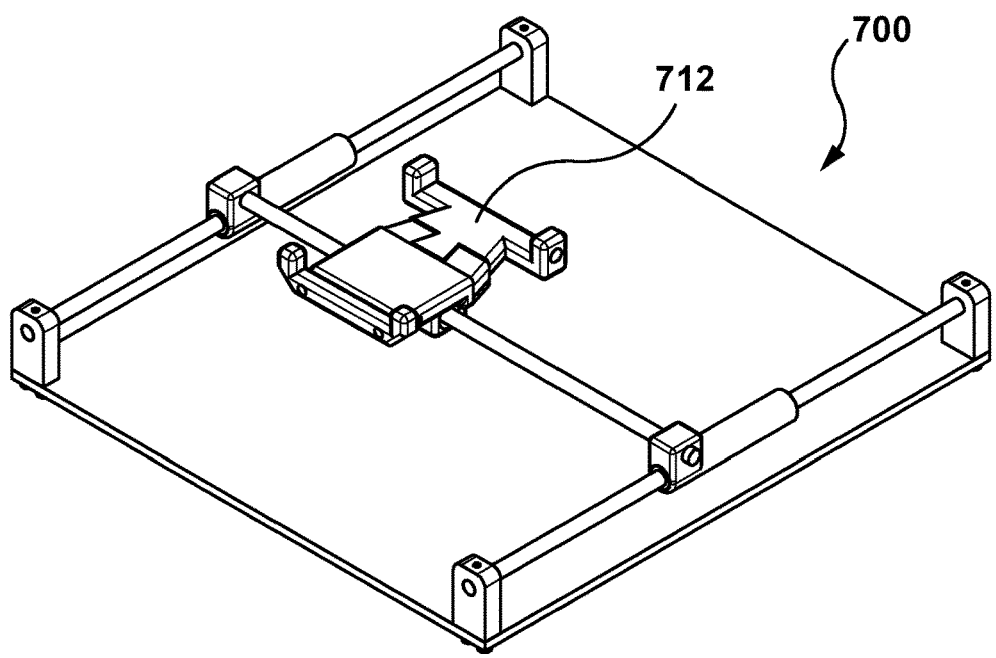
FIG. 9C is a schematic perspective view of the device of FIG. 9A.
Figure 9D:
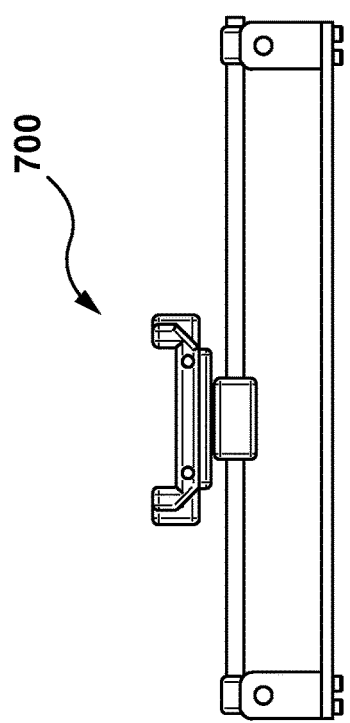
FIG. 9D is a schematic end view of the device of FIG. 9A.
Figure 9E:
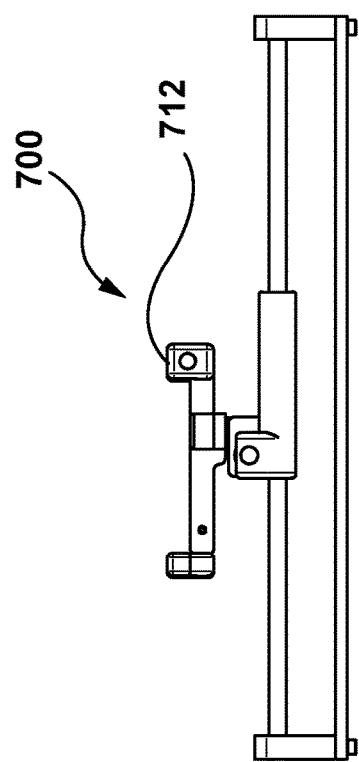
FIG. 9E is a schematic side view of the device of FIG. 9A.
Figure 9F:
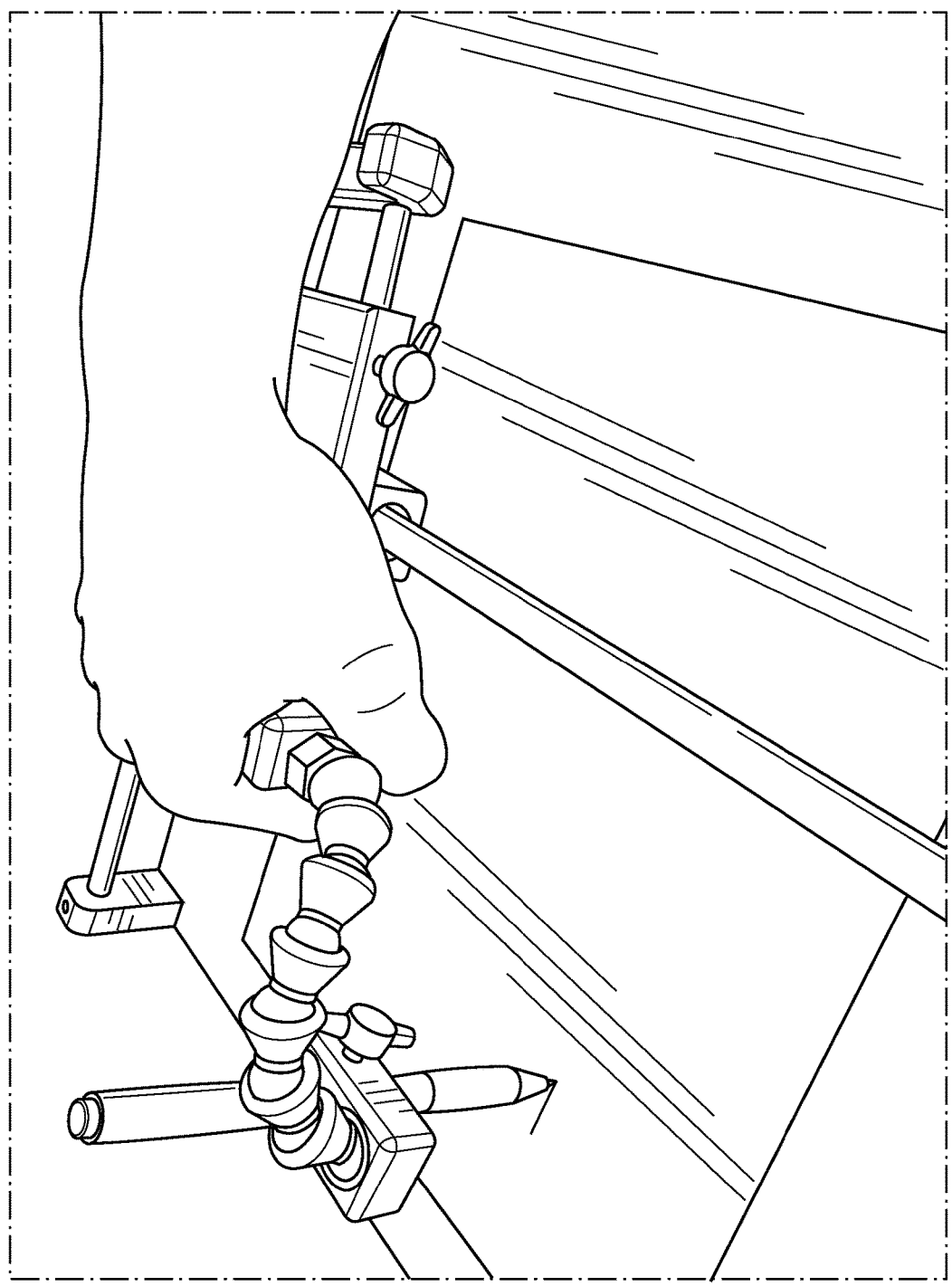
FIG. 9F is a perspective view of a user using the device of FIG. 9A.
Figure 10B:
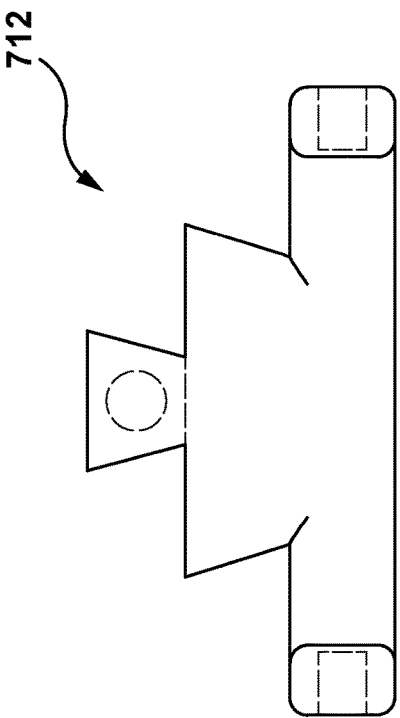
FIG. 10B is a front view of the hand support of FIG. 9A.
Figure 10D:
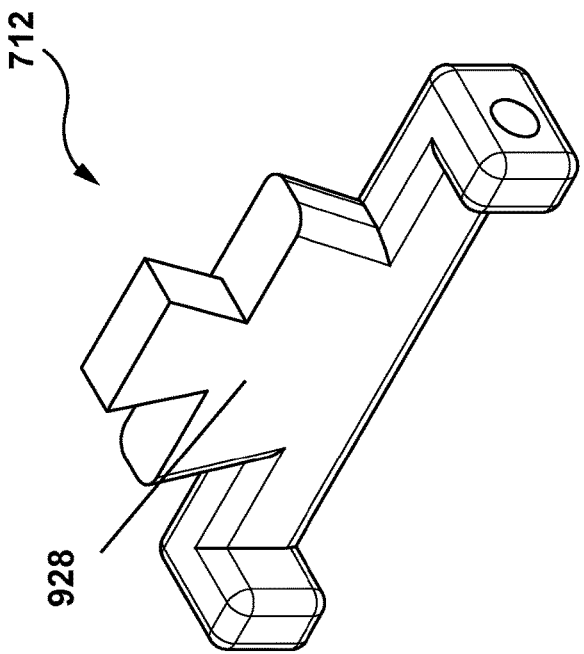
FIG. 10D is a perspective view of the hand support of FIG. 9A.
Figure 10A:
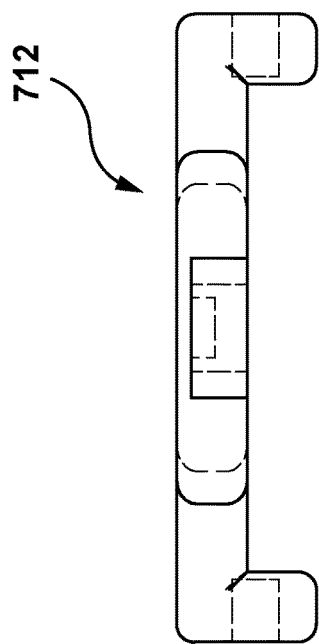
FIG. 10A is a top view of a hand support of the device of FIG. 9A, according to at least one embodiment.
Figure 10C:
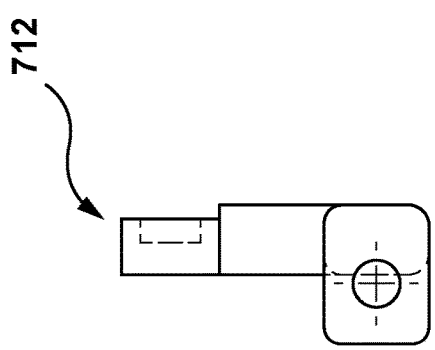
FIG. 10C is an end view of the hand support of FIG. 9A.
Figure 11C:
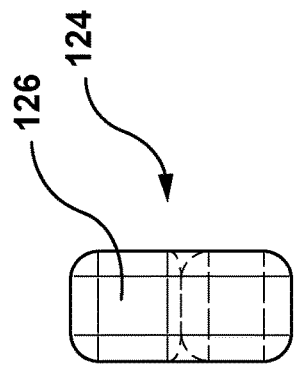
FIG. 11C is an end view of the wrist support of FIG. 11A.
Figure 11D:
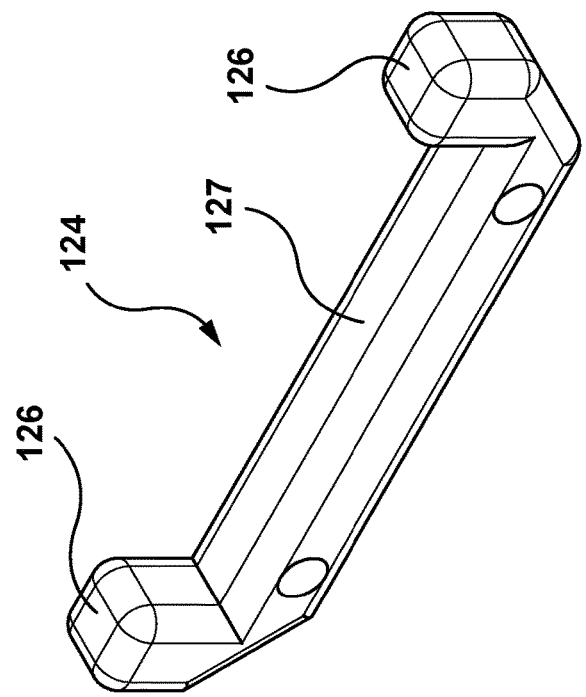
FIG. 11D is a perspective view of the wrist support of FIG. 11A.
Figure 11A:
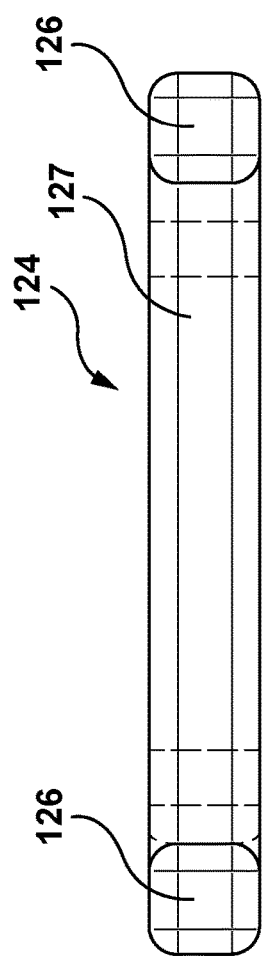
FIG. 11A is a top view of a wrist support of the device of FIG. 1A, according to at least one embodiment.
Figure 11B:
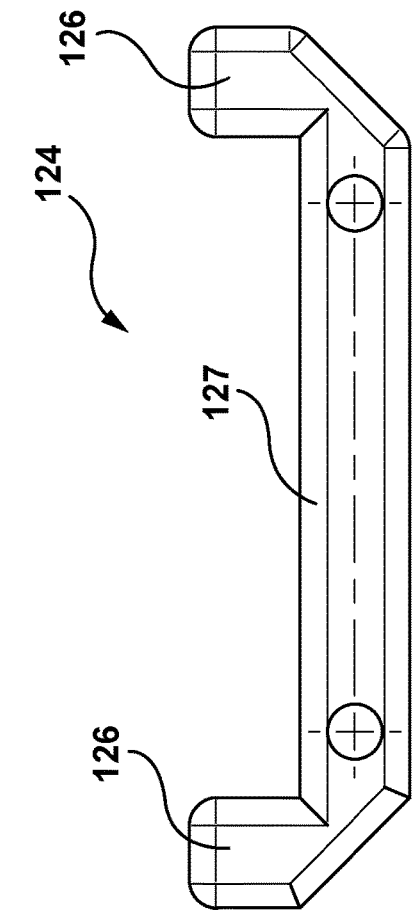
FIG. 11B is a front view of the wrist support of FIG. 11A.

Turning now to the figures, FIG. 1 shows a perspective view of a device 100 for assisting a user to manipulate an instrument 115 to interact with an object 101 resting on a surface, according to at least one embodiment. Device 100 includes a framework 103 and a wrist and hand support 108 coupled to the framework 103.

In some embodiments, framework 103 includes a base 102, two lateral supports 104a and 104b spaced apart from each other (e.g. positioned on opposed sides of the base 102), a crossing support 106 slidably coupled to each of the lateral supports 104a, 104b, respectively, and a hand and wrist support 108 coupled to the crossing support 106.

Base 102 is generally flat with a planar shape and provides for supporting an object 101 such as but not limited to a piece of paper, a booklet, a canvas, an electronic device, or the like for use with the device 100. For instance, as shown in FIG. 1, booklet 101 can be positioned on the base 102 below the crossing support 106. Base 102 may be made of any appropriate material, such as but not limited to a plastic, metal or the like. In some embodiments framework 103 may not include a base 102 and object 101 may rest directly on a surface such as a surface that is supporting framework 103.

Base 102 can generally have any geometric shape. In the embodiment shown in FIG. 1, base 102 has a generally rectangular shape with opposed sides 102a and 102b and opposed ends 102c and 102d. Herein, ends 102c and 102d may be referred to as a top end and a bottom end, respectively.

Lateral supports 104a and 104b are spaced apart from each other (e.g. on opposed sides of object 101) and, in embodiments where framework 103 includes a base 102, may be positioned on opposed sides of the base 102. Lateral supports 104a and 104b provide for supporting the crossing support 106 over the object 101 and for the crossing support 106 to slide longitudinally (i.e. lengthwise rather than across) between top end 102c and bottom end 102d of the base 102. One embodiment of a lateral support 104a is shown in FIGS. 2A-2C. In this embodiment, the lateral supports 104a and 104b are machined metal rods with a circular cross-section to provide for crossing support 106 to slide longitudinally between top end 102c and bottom end 102d of the base 102. In other embodiments, the lateral support 104a and 104b and/or the crossing support 106 may be any bar, rail, pole, shaft or tube and/or may have a different shape such as but not limited to a flattened shape (e.g. like that of a rail).

In the embodiment shown in FIG. 1, each end of each of the lateral supports 104a and 104b is fixedly coupled to a stand 116. Each stand 116 provides for the ends of the lateral supports to be coupled to the base 102 and be elevated above a top surface of the base 102. In the embodiment shown in FIG. 1, the stands 116 are each positioned in a corner of the base 102. Stands 116 can be made of any appropriate material for supporting the lateral supports above a top surface of the base 102, such as but not limited to aluminum or stainless steel.

In the embodiment shown in FIGS. 3A-3D, each stand 116 includes an aperture 117 sized to receive an end of a lateral support 104. Aperture 117 is vertically spaced from a bottom end 118 of the stand 116 by a distance A to provide for the lateral support to be supported above a top surface of the base 102.

Crossing support 106 is fixedly vertically spaced above the object 101. For instance, crossing support 106 may be vertically spaced above the object 101 by a distance of about 1 inch, or about 2 inches, or more than 2 inches. Crossing support 106 extends across the object 101. In embodiments where the framew2ork 103 includes a base 102, crossing support 106 extends between a first side 102a of the base 102 and a second side 102b of the base 102. Crossing support 106 may be a machined metal rod with a circular cross-section.

Crossing support 106 is slidably coupled to each of the lateral supports 104a and 104b. For instance, each end of crossing support 106 may be slidably coupled to one of the lateral supports 104a and 104b by a housing 120. One embodiment of a housing 120 is shown in FIGS. 4A to 4D. In this embodiment, each housing 120 includes one or more bearings (not shown) and is configured to receive a lateral support 104a, 104b and slide along an outer surface of the lateral support 104a, 104b. To receive lateral support 104a, 104b, housing 120 includes a first aperture 121 extending longitudinally along a length of the housing 120. First aperture 121 may include one or more bearings. Housing 120 is also configured to receive crossing support 106. To receive crossing support 106, housing 120 includes a second aperture 122. Second aperture 122 is generally perpendicular to first aperture 121. In the embodiment shown, second aperture 122 has a smaller diameter than first aperture 121 to provide for receiving the crossing support 106, which has a smaller diameter than the lateral supports 104a, 104b of the device 100 shown in FIG. 1.

Crossing support 106 defines a first axis AA (see FIG. 1) and is configured to slide longitudinally along the lateral supports 104a, 104b in a direction that is transverse to the first axis AA.

Hand and wrist support 108 includes a wrist plate 110 and a hand support 112 coupled to the wrist plate 110. In some embodiments, hand and wrist support 108 may also include an instrument retainer 114 configured to retain instrument 115. Instrument retainer 114 may be movably coupled to the hand support 112. In some embodiments, instrument retainer 114 may be a single piece that couples an instrument 115 to the hand support 112. In the embodiments shown in the figures, instrument retainer 114 includes a flexible linkage 113 coupled to a clamp 119.

Hand and wrist support 108 is configured to slide horizontally along the crossing member 106 and rotate about the crossing member 106. Hand and wrist support 108 is also vertically spaced above the object 101. In the embodiment shown in FIG. 1, hand and wrist support 108 is configured to slide along the crossing support 106 along the axis AA by a swivel 111. One embodiment of a swivel 111 is shown in FIGS. 5A to 5D.

Swivel 111 provides for the hand and wrist support 108 to be rotatably coupled to the crossing support 106 and to rotate about the axis AA defined by the crossing support 106. Rotation of the hand and wrist support 108 about the axis AA can provide for a user using the device 100 to raise and lower instrument 115 retained by the instrument retainer 114 (described below) relative to the object 101. For instance, when the instrument 114 is a writing instrument (e.g. such as but not limited to a pen, a pencil, a stylus, a paintbrush or the like), the user can rotate the hand and wrist support 108 about the crossing support 106 to raise a lower the writing instrument to write on an object 101 (as shown as an example in FIG. 1).

Swivel 111 includes a first aperture 125 extending along a width of the swivel and configured to receive the crossing support 106. First aperture 125 may also house one or more bearings. Swivel 111 also includes a second aperture 129 extending at least partially into the swivel 111. Second aperture 129 is configured to receive a fastener for securing the swivel 111 to wrist plate 110 (described below). Swivel 111 provides for the hand and wrist support 108 to rotate about the axis AA of the crossing support 106 and to slide horizontally along the crossing support 106.

Hand and wrist support 108 includes a wrist plate 110 for supporting a wrist of the user above the object 101. An embodiment of wrist plate 110 is shown in FIGS. 6A to 6D. Wrist plate 110 is coupled to hand support 112. In the embodiments shown in the FIGS., wrist plate 110 includes an upper portion 110a and a lower portion 110b. In some embodiments upper portion 110a may be coupled to swivel 111, such as via a fastener passing through aperture 131. In some embodiments, lower portion 110b may be coupled to connector 123, such as via a fastener passing through one or more of apertures 132. Wrist plate 110 is generally made of a rigid material, such as but not limited to aluminum.

One embodiment of connector 123 is shown in FIGS. 7A to 7D. Connector 123 is for coupling the wrist plate 110 to the hand support 112. Generally, connector 123 fixedly couples to the wrist plate 110 (e.g. via a fastener) and frictionally couples (e.g. without any fasteners) to the hand support 112. Frictionally coupling the connector 123 to the hand support 112 may provide for interchanging between various hand supports 112 (e.g. hand supports having different shapes and/or functions). In the embodiment shown in FIGS. 7A to 7D, connector 123 includes apertures 123a extending therethrough for receiving fasteners for fixedly coupling the connector 123 to wrist plate 110. In the embodiment shown in FIGS. 6A to 6D, connector 123 also includes a recess 137 for receiving a portion of the hand support 112 for frictionally coupling to the hand support 112.

Hand and wrist support 108 includes a hand support 112. Hand support 112 may be removably coupled to the wrist plate 110 (e.g. via connector 123) and is for supporting a hand of the user above the object 101 when the user is using the device 100. During use, the user holds the hand support 112 while manipulating instrument 115 coupled to the hand support 112, such as for example by instrument retainer 114.

The shape of the hand support 112 can be customized, for example to provide an ergonomic shape for the user depending on the user's condition. For instance, in the embodiment shown in FIG. 1, the hand support 112 has a semi-spherical or a spherical shape to provide for a user's hand to naturally and comfortably rest on an outer surface of the hand support 112. Hand support 112 is shown in greater detail in FIGS. 8A to 8D.

Specifically, the embodiment of hand support 112 shown in FIGS. 8A to 8D includes a protruding portion 128 for frictionally coupling to connector 123. Protruding portion 128 is generally sized and shaped to fit snuggly within recess 137 of connector 123.

Hand and wrist support 108 may also include an instrument retainer 114 (see FIG. 1A). In some embodiments, instrument retainer 114 may be a single piece that couples the instrument 115 to the hand support 112. In the embodiments shown in the figures, instrument retainer 114 includes a flexible linkage 113 coupled to a clamp 119. Instrument retainer 114 may be movably coupled (e.g. by a flexible linkage 113) to the hand support 112 for retaining an instrument 115.

In the embodiments shown, flexible linkage 113 provides for independently moving the instrument 115 relative to the hand piece 112 to adjust a position of the instrument 115 when changing the object 101 (e.g. paper, book canvas, computer, etc.) resting on the surface.

Clasp 119 (see FIG. 1A) may be any clasp, grip, handle or tightening mechanism for retaining an instrument 115 such as but not limited to a writing or marking instrument such as but not limited to a pen, a pencil, a stylus, a paintbrush or the like.

Hand support 112 may also be configured to provide for use by users having a dominant right hand or a dominant left hand. For instance, hand support 112 may include one or more apertures 138 (see FIG. 8A) for receiving instrument retainer 114 (e.g. flexible linkage 113) for coupling the instrument 115 to the hand support 112. In some embodiments, aperture 138 may be positioned to rest between a forefinger and a thumb of the user's right hand while the user is using the device 100. In some embodiments, aperture 138 may be positioned to rest between a forefinger and a thumb of the user's left hand while the user is using the device 100. This may provide for the instrument to be viewable to the user during use and may provide for the flexible linkage 113 to be positioned to not impede the user's fingers when the user's fingers are on the hand support 112 irrespective of whether the user is using their right hand or left hand.

FIGS. 9A to 9F shown another embodiment of a device 600 for assisting a user to manipulate an instrument 115 to interact with an object 101 resting on a surface. In the embodiment shown in FIGS. 9A to 9F, the hand support 712 has a shape that provides for a user's fingers to curl around an upper edge 713 of the hand support 712. An example of this is shown specifically in FIG. 9F. Also shown therein, hand support 712 may also be configured for use by users having a dominant right hand or a dominant left hand. For instance, hand support 712 may include an aperture 738 for receiving flexible linkage 113 at a position between a forefinger and a thumb of the user while the user is using the device 600.

Hand support 712 is shown in greater detail in FIGS. 10A to 10D. Hand support 712 also includes a protruding portion 928 for frictionally coupling to connector 123. Protruding portion 928 is also generally sized and shaped to fit snuggly within recess 137 of connector 123.

Hand support 112 (or 712) can be formed by 3D printing, for example, to provide customized shapes and/or geometries (e.g. ergonomic shapes) to accommodate different users with different physical conditions and/or limitations. Customizing the shape of the hand support 112 (or 712) may provide for decreasing hand fatigue and/or hand pain of the user while the uses device 100 (or device 600).

Hand and wrist support 108 may also include a wrist support member 124. One embodiment of a wrist support member 124 is shown in FIGS. 11A to 11D. Wrist support member 124 may include two upwardly extending protrusions 126 that are spaced apart from each other by a distance to provide for a user's wrist to rest between protrusions 126 on a body 127 of the wrist support member 124. Wrist support member 124 can be made from any material that provides comfort to a user's wrist during use of the device 100, such as but not limited to any polymeric or other cushioned material. In some embodiments, wrist support member 124 can be made of a polymer materials that can be 3D printed to provide for customizing its shape.

In the embodiments shown in the figures, the wrist support member 124 is positioned in a direction towards a bottom end of the framework 103 relative to the crossing support 106 and the hand support 112 is positioned in a direction towards a top end of the framework 103 relative to the crossing support 106.

Figure 12B:
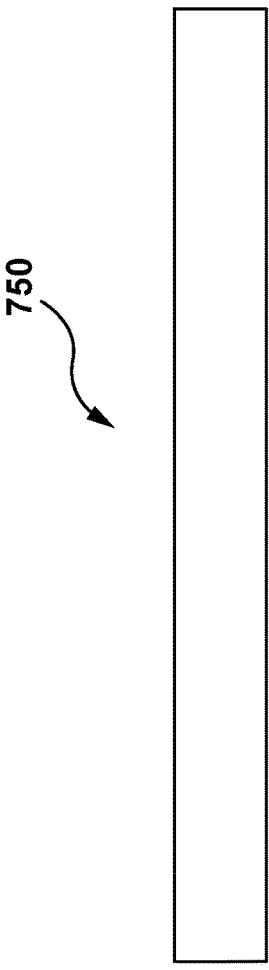
FIG. 12B is a side view of the wrist rod of FIG. 12A.
Figure 12C:
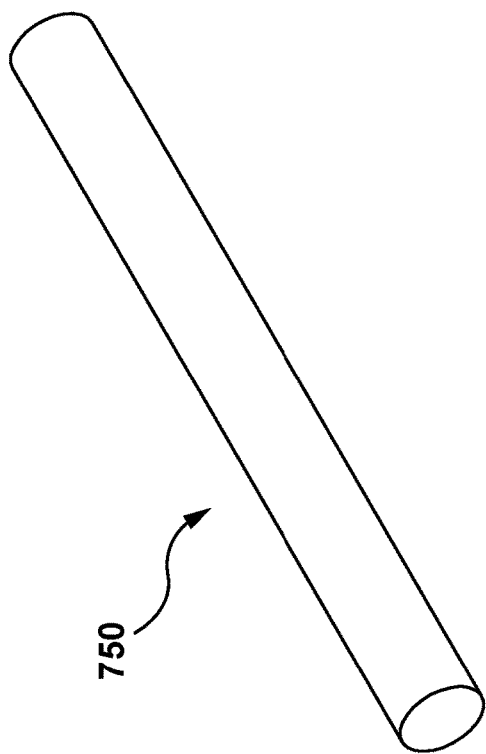
FIG. 12C is a perspective view of the wrist rod of FIG. 12A.
Figure 12A:
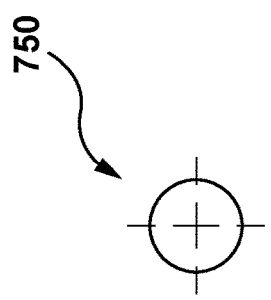
FIG. 12A is an end view of a wrist rod of the device of FIG. 9A, according to at least one embodiment.

In the embodiment of device 900 shown in FIGS. 9A to 9F, the wrist support member 124 is spaced from wrist plate 110 in a direction towards a bottom end of the framework 103. One or more rods 940 (see FIGS. 12A to 12C) support the wrist support member 124 to be spaced from the wrist plate 110. Rods 940 are generally made of a strong, rigid material such as but not limited to stainless steel.

Figure 13A:
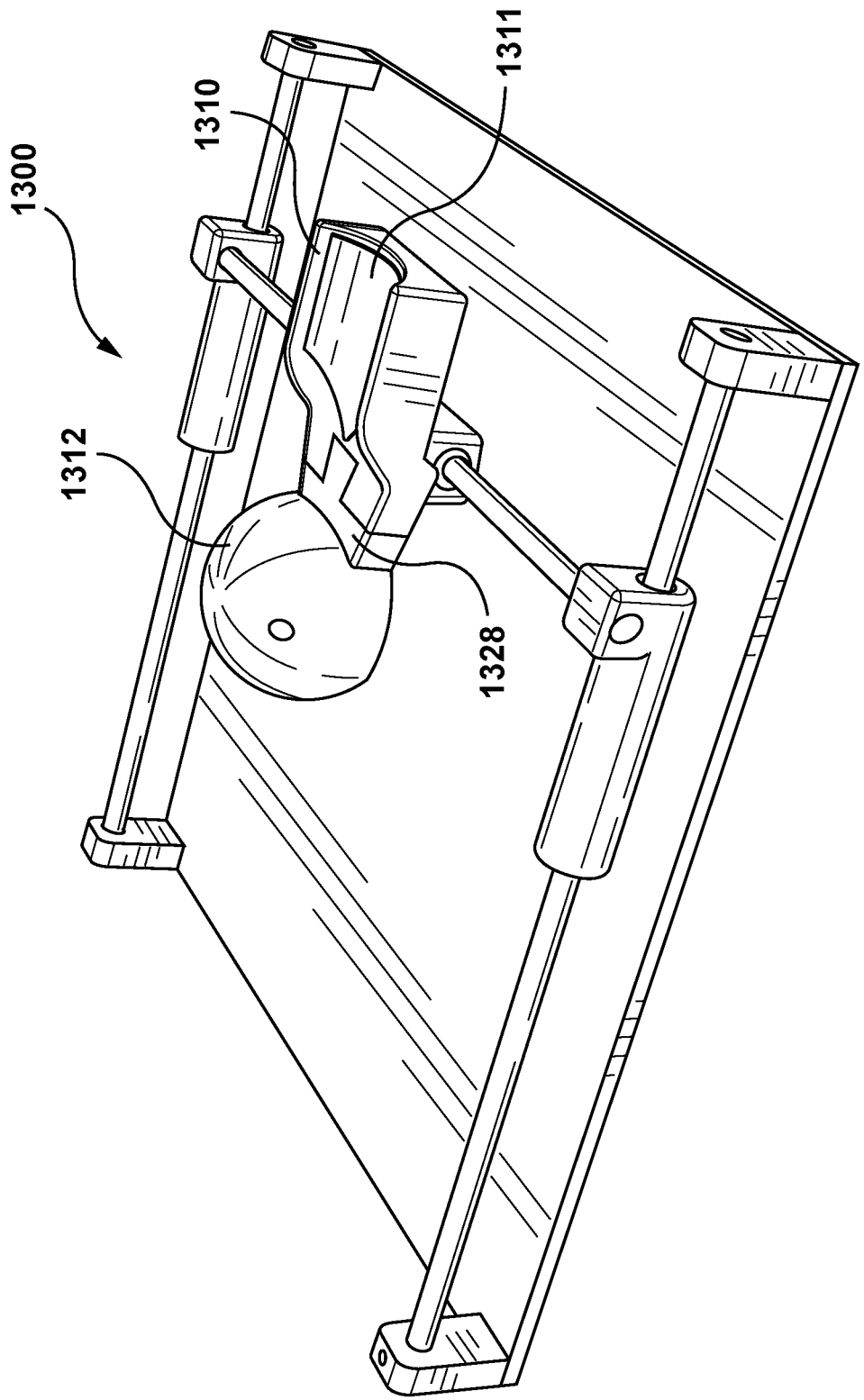
FIG. 13A is a perspective view of another device for assisting a user to manipulate an instrument to interact with an object resting on a surface, according to at least one embodiment.
Figure 13B:
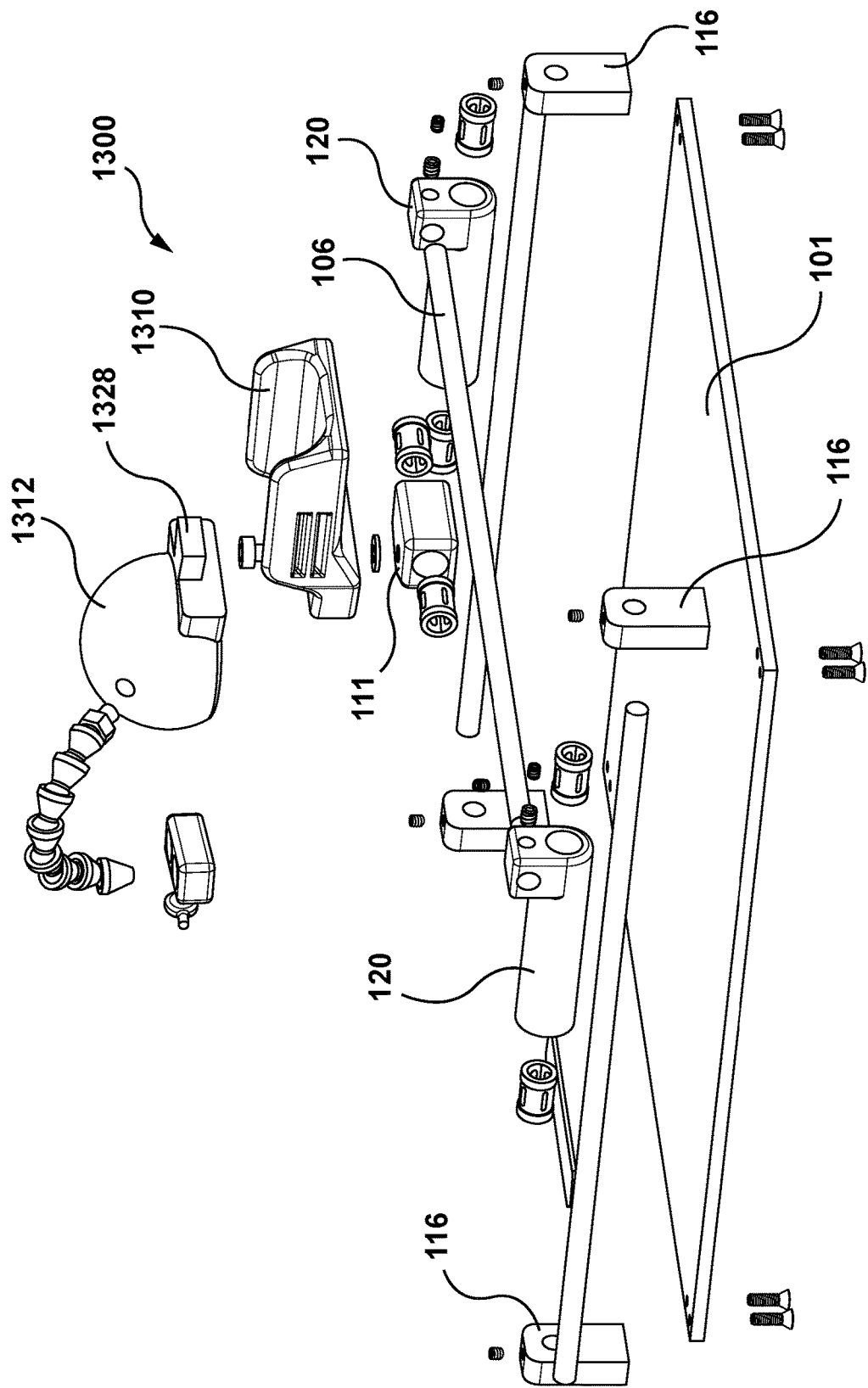
FIG. 13B is an exploded perspective view of the device for assisting a user to manipulate an instrument to interact with an object resting on a surface of FIG. 13A.
Figure 14A:
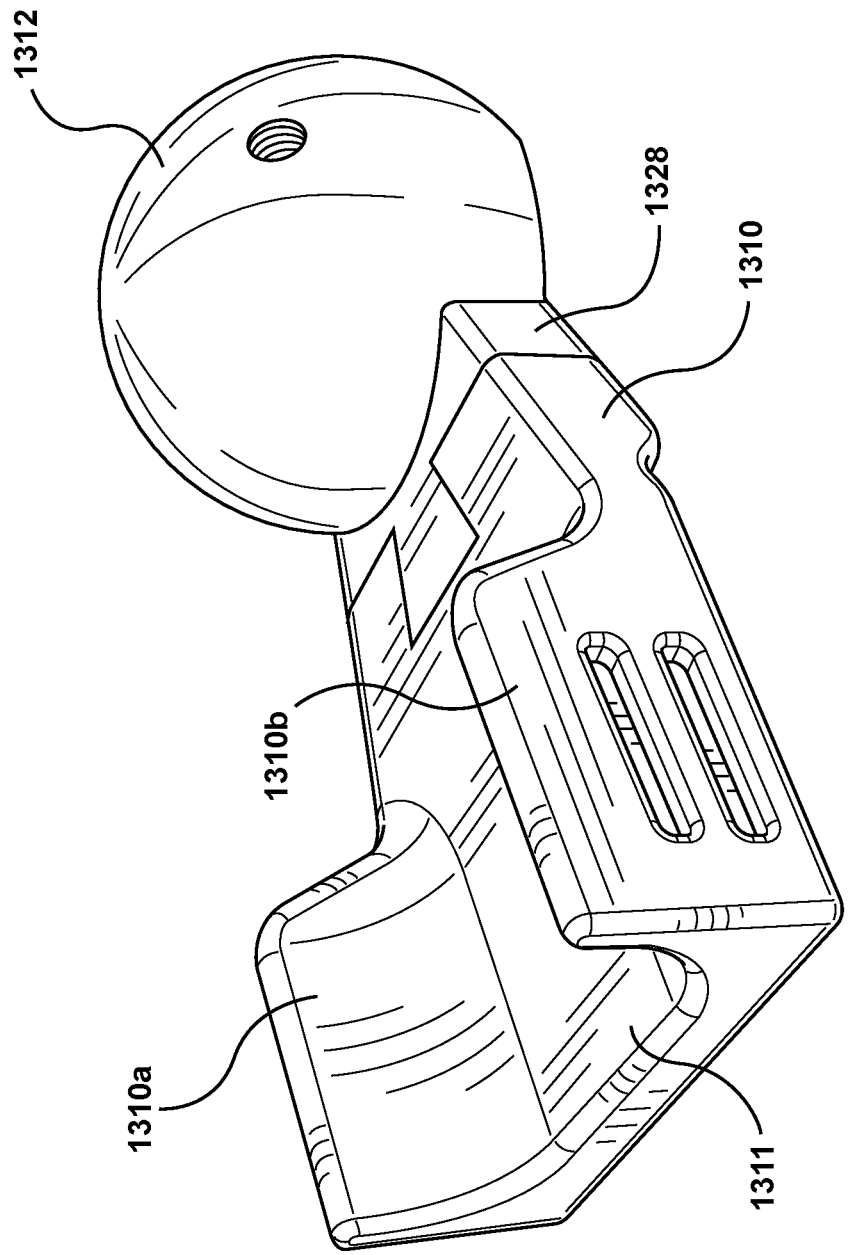
FIG. 14A is a perspective view from the rear of a wrist support and hand support of the device of FIG. 13A according to at least one embodiment.
Figure 14B:
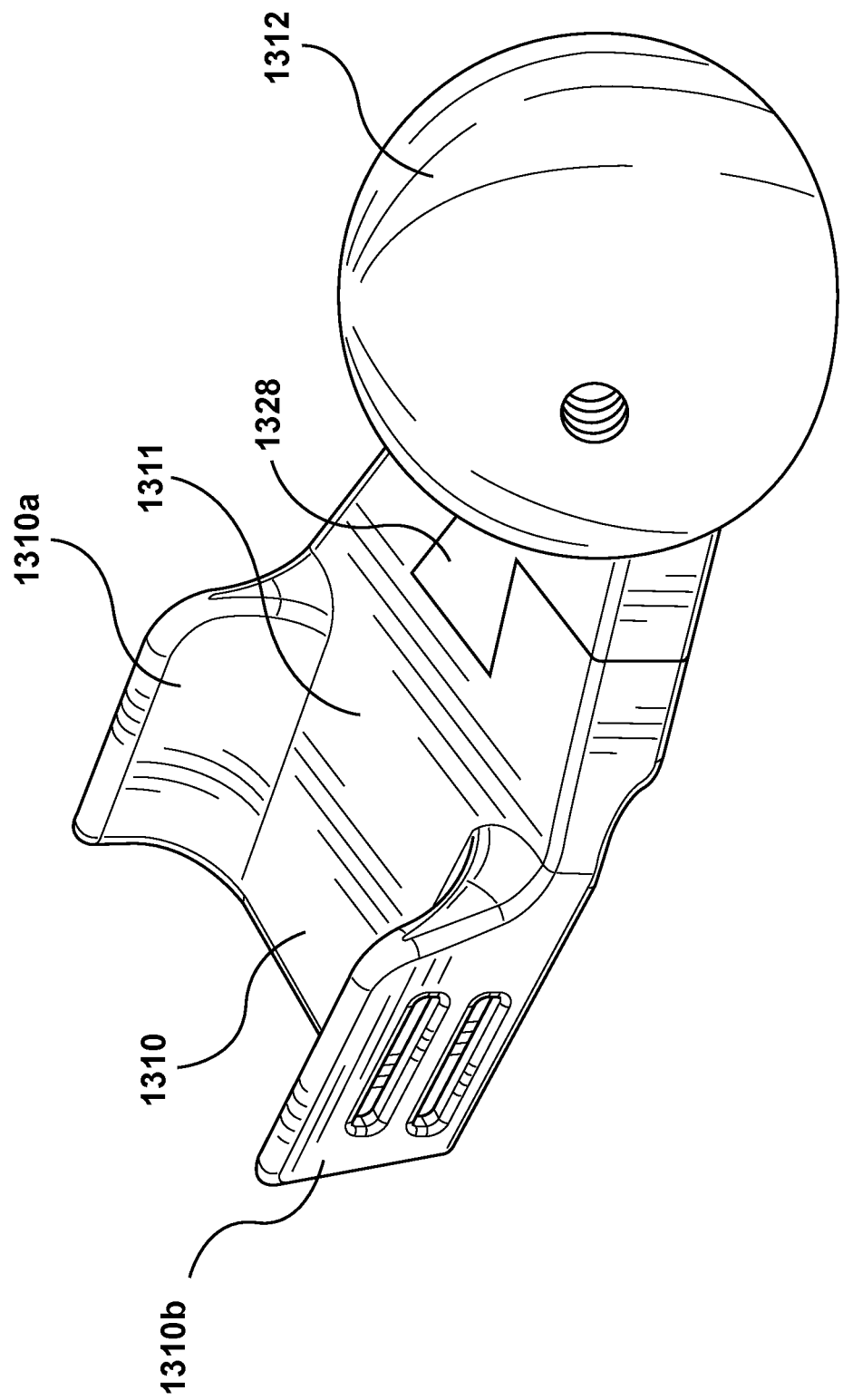
FIG. 14B is a perspective view from the front of the wrist support and hand support of FIG. 14A.

Turning to FIGS. 13A and 13B, illustrated therein is another embodiment of a device 1300 for assisting a user to manipulate an instrument to interact with an object resting on a surface. In the embodiment shown in FIGS. 13A and 13B, the hand support 1312 is coupled to a wrist support 1310 having an ergonomic design. Specifically, the wrist support 1310 includes opposed upwardly extending sides 1310a and 1310b, respectively, that are contoured to provide a smooth upper surface 1311 for supporting the wrist of a user. Upper surface 1311 may optionally be covered with a soft material, such as but not limited to foam.

In this embodiment, hand support 1312 is directly coupled to a wrist support 1310 by a protrusion 1328. Protrusion 1328 is generally sized and shaped to fit snuggly within a recess of wrist support 1310.

It should be noted that the wrist supports described herein (e.g. wrist support 1310) may also be configured to include a wrist strap (not shown). For instance, wrist support 1310 may include one or more apertures in opposed upwardly extending sides 1310a and 1310b to receive at least a portion of a wrist strap. A wrist strap may aid in retaining the wrist of a user of the device 1300 on the upper surface 1311 of wrist support 1310.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

What is claimed is:

1. A device for assisting a user to manipulate an instrument to interact with an object resting on a surface, the device comprising:
   a framework for resting on the surface; and
   a hand and wrist support coupled to the framework and coupled to the instrument and vertically spaced above the surface, the hand and wrist support being configured to slide horizontally and longitudinally along the framework and rotate about the framework to provide for the user to move the hand and wrist support to manipulate the instrument to interact with the object.

2. The device of claim 1, wherein the framework comprises:
   two lateral supports spaced apart from each other; and
   a crossing support coupled to each of the two lateral supports and coupled to the hand and wrist support, the crossing support being vertically spaced above the surface.

3. The device of claim 2, wherein the crossing support is configured to slide horizontally and longitudinally along the two lateral supports.

4. The device of claim 2, wherein the crossing support defines a first axis and the hand and wrist support is configured to slide along the crossing support.

5. The device of claim 4, wherein the hand and wrist support is configured to rotate about the crossing support.

6. The device of claim 5, further comprising a swivel coupled to the hand and wrist support and the crossing support to provide for the hand and wrist support to rotate about the crossing support.

7. The device of claim 2, wherein the framework further comprises a base for resting on the surface and supporting the object.

8. The device of claim 1, wherein the hand and wrist support includes:
   a wrist support coupled to the crossing support for supporting a wrist of the user above the surface; and
   a hand support coupled to the wrist support for supporting a hand of the user above the surface.

9. The device of claim 8, wherein the hand and wrist support further includes an instrument retainer for movably coupling the instrument to the hand support.

10. The device of claim 9, wherein the instrument retainer includes a flexible linkage coupled to the hand support and a clamp coupled to the flexible linkage, the clamp configured to retain the instrument.

11. The device of claim 7, wherein the hand support is shaped to provide for a user to curl their fingers around a top end of the hand support to grip the hand support.

12. The device of claim 7, wherein the hand piece has a semi-spherical shape.

13. The device of claim 7, wherein the hand support is releasably coupled to the wrist support.

14. The device of claim 13, wherein the hand support is releasably coupled to the wrist support by friction.

15. The device of claim 14, wherein the wrist support includes a recess and the hand support includes a protruding portion, the protruding portion being sized and shaped to fit within the recess to releasably couple the hand support to the wrist support by friction.

* * * * *